(12) United States Patent
Dubois et al.

(10) Patent No.: US 10,287,238 B2
(45) Date of Patent: May 14, 2019

(54) GAS-PHASE AND LIQUID-GAS-PHASE NITRILATION PROCESS

(71) Applicants: Arkema France, Colombes (FR); Centre National De La Recherche Scientifique (CNRS), Paris (FR); Universite Claude Bernard Lyon 1, Villeurbanne (FR)

(72) Inventors: Jean-Luc Dubois, Millery (FR); Adrien Mekki-Berrada, Paris (FR); Aline Auroux, Villeurbanne (FR); Simona Bennici, Villeurbanne (FR)

(73) Assignee: Arkema France, Colombes (FR)

( * ) Notice: Subject to any disclaimer, the term of this patent is extended or adjusted under 35 U.S.C. 154(b) by 160 days.

(21) Appl. No.: 14/769,312

(22) PCT Filed: Feb. 19, 2014

(86) PCT No.: PCT/EP2014/053213
§ 371 (c)(1),
(2) Date: Aug. 20, 2015

(87) PCT Pub. No.: WO2014/128154
PCT Pub. Date: Aug. 28, 2014

(65) Prior Publication Data
US 2016/0016153 A1    Jan. 21, 2016

(30) Foreign Application Priority Data
Feb. 20, 2013 (FR) ..................... 13 51432

(51) Int. Cl.
| | | |
|---|---|---|
| C07C 253/22 | (2006.01) | |
| B01J 21/06 | (2006.01) | |
| B01J 23/745 | (2006.01) | |
| B01J 23/835 | (2006.01) | |
| B01J 23/847 | (2006.01) | |
| B01J 35/10 | (2006.01) | |
| B01J 37/04 | (2006.01) | |
| B01J 35/00 | (2006.01) | |

(52) U.S. Cl.
CPC .......... *C07C 253/22* (2013.01); *B01J 21/066* (2013.01); *B01J 23/745* (2013.01); *B01J 23/835* (2013.01); *B01J 23/8474* (2013.01); *B01J 23/8476* (2013.01); *B01J 35/108* (2013.01); *B01J 35/1014* (2013.01); *B01J 35/1019* (2013.01); *B01J 35/1057* (2013.01); *B01J 35/1061* (2013.01); *B01J 37/04* (2013.01); *B01J 35/0006* (2013.01)

(58) Field of Classification Search
CPC .................................................. C07C 253/22
See application file for complete search history.

(56) References Cited

U.S. PATENT DOCUMENTS

| | | | | |
|---|---|---|---|---|
| 2,794,043 A * | 5/1957 | Jansen | ............... | C07C 253/22 422/429 |
| 3,012,060 A * | 12/1961 | Aries | ................ | C07C 253/22 558/311 |
| 3,661,970 A * | 5/1972 | Canavan | ............ | C07C 253/22 558/313 |
| 4,575,434 A | 3/1986 | Frank | | |
| 4,801,730 A | 1/1989 | Stuhler | | |
| 6,005,134 A * | 12/1999 | Terasaka | ............ | C07C 253/22 558/311 |
| 6,080,891 A | 6/2000 | Terasaka | | |
| 7,259,274 B2 | 8/2007 | Terasaka | | |
| 8,697,401 B2 * | 4/2014 | Dubois | ............. | C07C 51/353 435/128 |
| 8,748,651 B2 * | 6/2014 | Dubois | ............. | C07C 227/04 560/155 |
| 8,835,661 B2 * | 9/2014 | Couturier | .......... | C07C 227/04 554/69 |
| 8,884,041 B2 * | 11/2014 | Couturier | .......... | C07C 227/04 554/114 |
| 8,927,746 B2 * | 1/2015 | Dubois | ............. | C07C 227/16 554/114 |

(Continued)

FOREIGN PATENT DOCUMENTS

| | | |
|---|---|---|
| FR | 2465714 | 3/1981 |
| GB | 2067197 | 5/1983 |

(Continued)

OTHER PUBLICATIONS

CAS Entry for Prnazarov et al. Izvestiya Ministerstva Nauki—Akademii Nauk Respubliki Kazakhstan, Seriya Khimicheskaya (1996), (3), 38-42.*
Machine translation of JP 04208260 A, obtained from https://worldwide.espacenet.com/ on Sep. 26, 2017.*
International Search Report for International Application No. PCT/EP2014/053213 dated Apr. 2, 2014.

*Primary Examiner* — Matthew P Coughlin
(74) *Attorney, Agent, or Firm* — RatnerPrestia

(57) ABSTRACT

A process for the nitrilation of a fatty acid or of a fatty acid ester, which is optionally unsaturated, by reacting the fatty acid or fatty acid ester with ammonia in a reactor operating continuously in the gas phase or in the mixed gas-liquid phase in a temperature range of from 180 to 400° C., in the presence of a solid catalyst comprising at least one metal oxide, the metal of which belongs to column 8 of the periodic table, as a mixture with at least one metal oxide chosen from aluminum oxides, zirconium oxides, niobium oxides, tantalum oxides and tin oxides, the metal oxide(s), the metal of which belongs to column 8, being present in a volume ratio of 0.1 to 0.6 relative to the volume of the mixture of all the oxides.

20 Claims, 2 Drawing Sheets

(56) References Cited

U.S. PATENT DOCUMENTS

| | | | |
|---|---|---|---|
| 9,035,079 B2* | 5/2015 | Brandhorst | ........... C07C 253/22 554/134 |
| 2005/0178658 A1 | 8/2005 | Nguyen | |
| 2010/0094057 A1 | 4/2010 | Oftring | |
| 2011/0224454 A1* | 9/2011 | Dubois | ................ C07C 227/04 560/155 |

FOREIGN PATENT DOCUMENTS

| | | |
|---|---|---|
| JP | 5690250 | 7/1981 |
| JP | 04208260 A * | 7/1992 |
| JP | 04283549 | 10/1992 |
| JP | 10195035 | 7/1998 |
| JP | 200016977 | 1/2000 |
| JP | 2009240874 | 10/2009 |
| KR | 20120105866 | 9/2012 |
| WO | 2013030481 | 3/2013 |

* cited by examiner

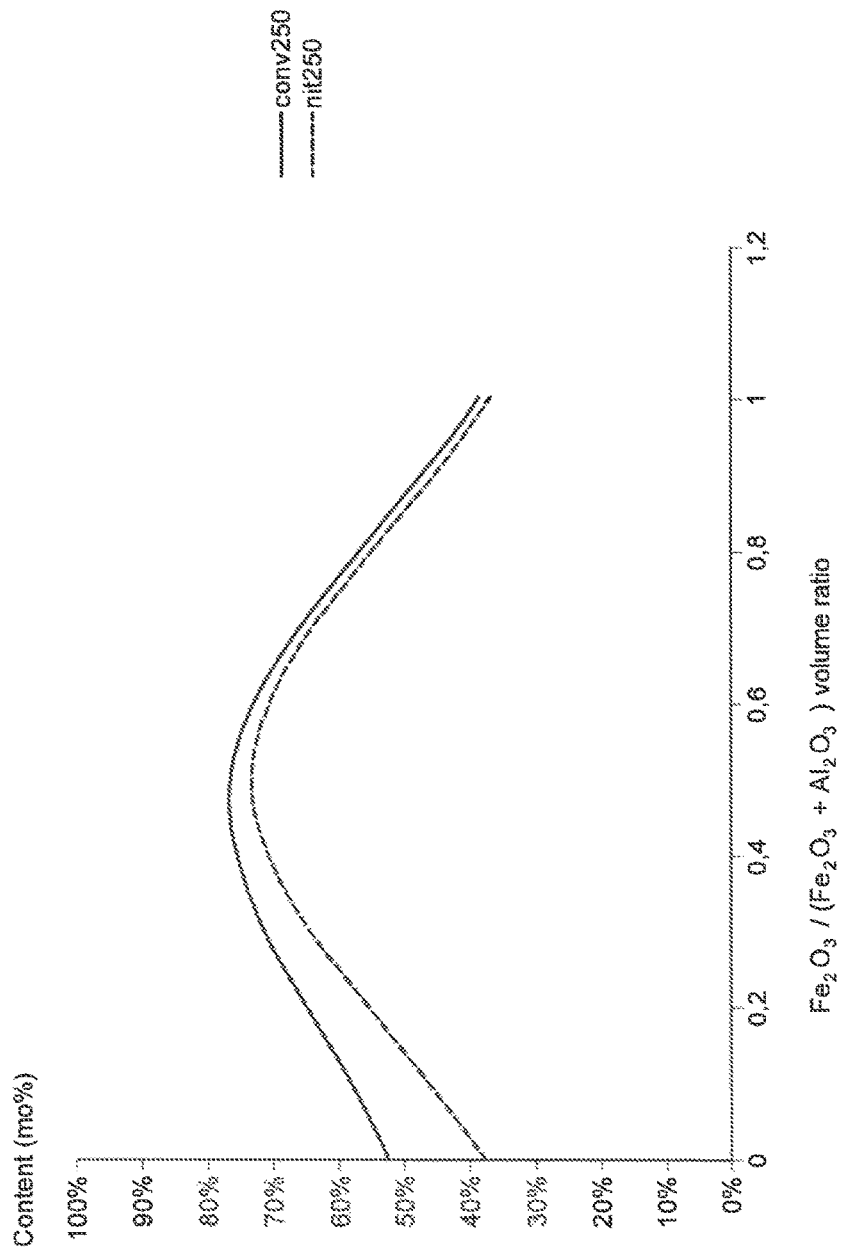

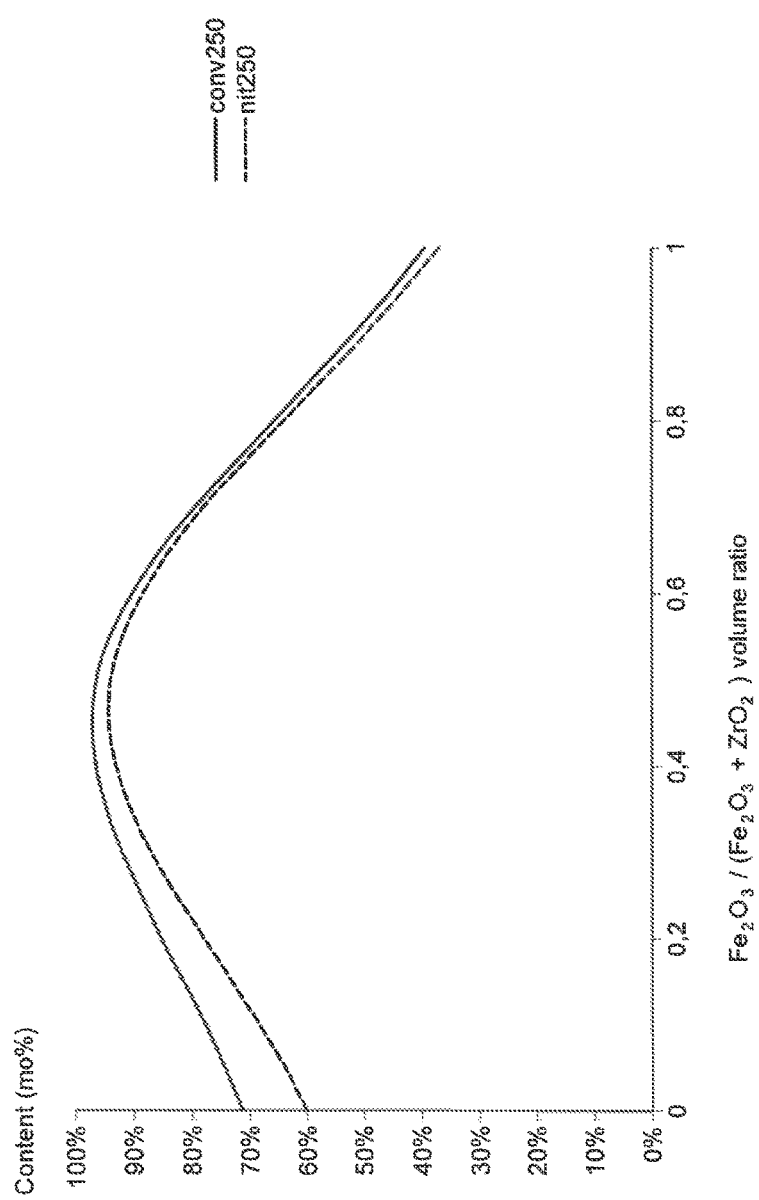

GAS-PHASE AND LIQUID-GAS-PHASE NITRILATION PROCESS

CROSS-REFERENCE TO RELATED APPLICATIONS

This application is a national phase of International Application No. PCT/EP2014/053213, filed Feb. 19, 2014, which claims priority from French Application No. 1351432, filed Feb. 20, 2013.

The work which led to this invention received financial support from the European Union in the context of Framework Program 7 (FP7/2007-2013) under project No. 241718 EUROBIOREF.

FIELD OF THE INVENTION

The invention is directed toward a process for nitrilation in the gas phase and in the mixed liquid-gas phase starting from fatty acid esters or from fatty acids using a specific solid catalyst based on a mixture of metal oxides. The invention also relates to a specific catalyst, to the process for the preparation thereof, and also to the use thereof.

DESCRIPTION OF THE RELATED ART

Processes for producing nitriles and/or fatty amines from fatty acids extracted from vegetable or animal oils are known. This process is described in the Kirk-Othmer Encyclopedia Vol 2, 4$^{th}$ Edition, page 411. The fatty amine is obtained in several steps. The first step consists of a methanolysis or hydrolysis of a vegetable oil or of an animal fat producing, respectively, the methyl ester of a fatty acid or a fatty acid. The methyl ester of the fatty acid can then be hydrolyzed to form the fatty acid. Next, the fatty acid is converted to nitrile by reaction with ammonia, and finally to amine by hydrogenation of the resulting nitrile.

The current change in terms of the environment is resulting, in the chemistry field, in the exploitation of natural raw materials originating from a renewable source being favored. This is why some research-development studies have been taken up again in order to industrially develop processes using fatty acids/esters as raw material for producing these nitriles.

SUMMARY OF THE INVENTION

The invention relates to a process for the nitrilation of the acid function or else of the ester function, depending on the reagent used, which is optionally unsaturated.

The reaction scheme for the synthesis of nitriles from a fatty acid can be summarized in the following way:

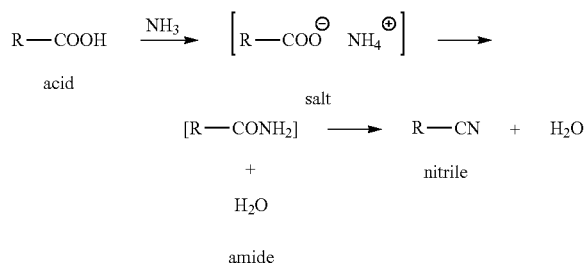

For the purposes of the present invention, the term "nitrilation" is intended to mean a reaction between a fatty acid or fatty acid ester and ammonia resulting in the conversion, respectively, of the $CO_2H$ or $CO_2R$ function to a CN function. This nitrilation reaction is also called ammoniation, since this reaction involves ammonia.

There are 2 types of processes based on this reaction scheme: a liquid-phase (generally batch) process and a vapor-phase (generally continuous) process.

In the liquid-phase batch process, the fatty acid or a mixture of fatty acids is loaded with a catalyst, which is generally a metal oxide, and most commonly zinc oxide. The reaction medium is brought to approximately 150° C. with stirring, then the introduction of gaseous ammonia is begun. In a first step, an ammonium salt or ammonium soap is formed. The temperature of the reaction medium is then brought to around 250° C.-300° C., still with the introduction of ammonia. The ammonium salt is converted into amide with release of a first water molecule. Then, in a second step and with the use of the catalyst, the amide is converted to nitrile with the formation of a second water molecule. This formed water is continuously removed from the reactor while entraining the ammonia which is not reacted and a small amount of fatty chains among the lightest. The liquid-phase processes, using batch reactors, require very long reaction times, in particular of several hours.

In the gas-phase (continuous) process, the feedstock is vaporized and brought into contact with ammonia, the temperature of which is between 250° C. and 600° C., in the presence of a catalyst. This catalyst is generally chosen from the family of metal oxides consisting of the oxides of metals, taken alone or as a mixture, such as Zr, Ta, Ga, In, Sc, Nb, Hf, Fe, Zn or Sn or alumina, a thorium oxide, and in particular doped alumina. The gas-phase processes are carried out continuously at a temperature of about 300° C., and under these conditions, the contact times are about a few seconds on the catalyst. Nevertheless, as soon as the temperature decreases, with the known catalysts, the conversions drop, and it is then necessary to increase the average contact time in order to return to high conversions.

These reactions, in their various forms, are mentioned in the Ullmann Encyclopédies vol. A2, page 20 and the Kirk Othmer Encyclopedia vol. 2 pages 411-412, and have been the subject of numerous patents filed in particular by the company KAO. Mention may be made of patents U.S. Pat. Nos. 6,005,134, 6,080,891 and 7,259,274, which describe the liquid-phase synthesis of aliphatic nitriles from fatty acids in the presence of a titanium catalyst. For the same applicant and for the same type of process, Japanese applications No. 11-117990 (Apr. 26, 1999) with a niobium catalyst and No. 9-4965 (Jan. 14, 1997) with a zirconium catalyst may be noted. Mention may also be made of a U.S. Pat. No. 4,801,730 which describes the liquid-phase nitrilation of glycerides and a Japanese application in the name of Lion Corp of Mar. 13, 1991 (Publication No. JP 4283549) which is directed toward the gas-phase synthesis of nitrile.

On the occasion of the studies it has carried out, the applicant has observed that the nitrilation step plays an important role, in particular when it is carried out on an ω-unsaturated acid. This is because the location of the double bond at the chain end and which is therefore barely protected, leads to the formation of isomers subsequent to the shift of the double bond. Having observed these phenomena, the applicant has noted that this drawback can be greatly limited by working with the ester rather than the corresponding acid, which makes it possible to carry out the process under "milder" conditions. This is because, since the boiling point of the ester is lower than that of the corresponding acid, it is possible to achieve higher vapor pressures with the ester. In addition, by carrying out the reaction in a continuously operating reactor, either in the gas phase or in the mixed liquid-gas phase, the residence time of the reagents in contact with the catalysts being much shorter than in the conventional liquid (batch) phase makes it possible to limit the isomerization during the process.

However, it has been noted that, even starting from an ester, the reaction results in the formation of isomers.

It is important to control this nitrilation step, and in particular when the following step is a metathesis or hydroformylation step. This is because said steps relate to the conversion of the double bond. Thus, when the nitrilation reaction results in the formation of several nitriles bearing double bonds at different positions on the fatty chain, the metathesis or hydroformylation reaction will necessarily result in unwanted by-products, resulting from this metathesis or hydroformylation reaction on the unwanted isomers of the nitrile. Consequently, for this type of synthesis, it is essential that the double bond does not migrate on the carbon chain.

Furthermore, there is still the need to search for operating conditions which result in a better degree of conversion and a better yield.

Indeed, it has been observed that, when the reaction temperature decreases, the level of amide, i.e. the intermediate compound, is greater.

Likewise, it has been observed that, when the reagent is methyl ester, N-methylated amide forms as intermediate compound, the formation of this intermediate amide blocking the nitrilation. Furthermore, this impurity limits the potential applications of the nitriles thus obtained.

Thus, a gas-phase or mixed liquid-gas phase nitrilation process which is more effective, whether the reagent is a saturated or unsaturated acid or ester, is sought. The objective sought is the obtaining of a process which results in an excellent degree of conversion, with an excellent yield, while decreasing the content of by-products resulting from the migration of the double bond, when the reagent used is unsaturated, while decreasing the content of by-products resulting from the methylation of the intermediate amide, when the reagent used is a methyl ester, and reducing the content of the intermediate amide.

Finally, a process which is less expensive in terms of energy and of catalyst used is sought.

A subject of the invention is a process for the nitrilation of a fatty acid or of a fatty acid ester, which is optionally unsaturated, by reacting ammonia in a reactor operating continuously in the gas phase or in the mixed gas-liquid phase in a temperature range of from 180 to 400° C., in the presence of a solid catalyst comprising:

at least one metal oxide, the metal of which belongs to column 8 of the periodic table, as a mixture with at least one metal oxide chosen from aluminum oxides, zirconium oxides, niobium oxides, tantalum oxides and tin oxides, the metal oxide(s), the metal of which belongs to column 8, being present in a volume ratio of 0.1 to 0.6 relative to the volume of the mixture of all the metal oxides.

Indeed, it has been observed that the use of these particular catalysts results in the nitrilation of the reagents in an extremely short average contact time. For example, the nitrilation of 1.6 g/h of lauric acid for a bed of 1.5 ml (≈1-2 g of catalyst) of ammonia, is carried out in 4.5 seconds for temperatures ranging from 200° C. to 300° C. These kinetics should be put alongside the 8 to 10 hours required for liquid-phase nitrilation in a batch reactor. These kinetics obtained at a relatively low temperature are surprising, as are the yield and the conversion of this nitrilation reaction under such operating conditions.

Furthermore, an absence of isomerization of the double bond during the reaction for nitrilation of methyl undecenoate, during a short contact time at relatively low temperatures has been observed. It would appear that the double bond does not have the time or the energy required to migrate along the carbon chain of the acid or of the ester.

Finally, yields have been observed that are much better for this nitrilation reaction, for example for the iron oxide and zirconium oxide pair and for zirconia alone, both at 200° C. and at 250° C. Since the $Fe_2O_3/ZrO_2$ mixture is much less expensive than zirconia alone, this result shows that the process is economically advantageous.

The invention also relates to a solid catalyst comprising at least one metal oxide, the metal of which belongs to column 8 of the periodic table, as a mixture with at least one metal oxide chosen from aluminum oxides, zirconium oxides, niobium oxides, tantalum oxides and tin oxides, the metal oxide(s), the metal of which belongs to column 8, being present in a volume ratio of 0.1 to 0.6 relative to the volume of the mixture of all the metal oxides.

The invention relates to the process for preparing this catalyst, and also to the use of this catalyst in nitrilation processes.

Other characteristics, aspects, subjects and advantages of the present invention will emerge more clearly on reading the description and the examples which follow.

Furthermore, any range of values denoted by the expression "between a and b" represents the range of values of from more than a to less than b (i.e. limits a and b excluded), whereas any range of values denoted by the expression "from a to b" signifies the range of values from a up to b (i.e. including the strict limits a and b).

BRIEF DESCRIPTION OF THE FIGURES

FIGS. 1 and 2 illustrate certain of the experimental results obtained, as described in the Examples.

DESCRIPTION OF CERTAIN EMBODIMENTS OF THE INVENTION

For the purposes of the present invention, the term "mixed gas-liquid phase" is intended to mean a process using a mixed gas-liquid fluid including a liquid as continuous phase and a gas as dispersed phase or else a liquid as dispersed phase and a gas as continuous phase. In a mode in which liquid descends on a catalyst in a fixed bed, there is a trickle-bed configuration, in a mode in which liquid rises and catalyst is in a fixed bed, there is an immersed-bed configuration. The reactor can also operate in fluidized-bed mode. In this configuration, the catalyst is kept fluidized not only by the gas stream, but also by the vaporization of liquid feedstock which thus generates a large volume of gas.

Nitrilation Process

The invention relates to a process for the nitrilation of a fatty acid or of a fatty acid ester, which is optionally unsaturated, by reacting ammonia in a reactor operating continuously in the gas phase or in the mixed gas-liquid phase in a temperature range of from 180 to 400° C., in the presence of a solid catalyst comprising at least one metal oxide, the metal of which belongs to column 8 of the periodic table, as a mixture with at least one metal oxide chosen from aluminum oxides, zirconium oxides, niobium oxides, tantalum oxides and tin oxides, the metal oxide(s), the metal of which belongs to column 8, being present in a volume ratio of 0.1 to 0.6 relative to the volume of the mixture of all the oxides.

The reagents of the nitrilation process according to the invention may be fatty acids or esters, which are optionally unsaturated, preferably ω-unsaturated.

For the purpose of the present invention, the term "fatty" is intended to mean an acid or an ester comprising a saturated or unsaturated, linear carbon chain comprising from 8 to 36 carbon atoms. Preferably, the acids and esters that are of use for the process of the invention have the following formula:

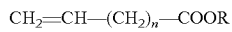

in which n represents the integer 7 or 8 and

R represents either a hydrogen atom or an alkyl radical comprising 1 to 4 carbon atoms.

Preferably, the process of the invention uses, as feedstock, ω-unsaturated acids or esters comprising either 10 carbon atoms or 11 carbon atoms per molecule. The first, in particular methyl 9-decenoate, are sold in ester form by the company Elevance Renewable Sciences. The second, in particular methyl 10-undecenoate, are produced by the company Arkema in the context of its castor oil-based process, methyl undecylenate being obtained after pyrolysis.

The nitrilation step is carried out in a reactor operating continuously, i.e. in which the reagents, whether they are of gas, solid or liquid origin, are introduced (and the products extracted) into the reactor continuously according to predetermined flow rates.

The process for the nitrilation of the fatty acids and the esters is carried out at a reaction temperature ranging from 180 to 400° C., and preferably from 200 to 300° C. and more preferably from 200 to 250° C. The feedstock of the fatty acids or esters, which are optionally unsaturated, is vaporized and brought to a temperature ranging from 180 to 350° C. on contact with the ammonia, the introduction temperature of which ranges from 150 to 600° C.

The pressure exerted in the reactor can range from 0.1 to 10 atmospheres (absolute), and preferably from 0.5 to 5 atm, and even more preferably from 1 to 3 atm.

The $NH_3$/fatty ester or $NH_3$/fatty acid molar ratio of the reagents can range from 1 to 50, preferably from 3 to 30, and even more preferably from 5 to 20.

In the Pure Gas Phase

In a first embodiment, the two reagents can be introduced into the reactor in the gas state (pure gas phase).

The fatty acid or the fatty acid ester, which is optionally unsaturated, is vaporized and brought to a temperature ranging from 180 to 350° C. on contact with the ammonia, the introduction temperature of which ranges from 150 to 600° C., and under a pressure ranging from 0.1 to 10 atmospheres (absolute), preferably from 0.5 to 5 atmospheres and even more preferably from 1 to 3 atmospheres.

The flow rates for introducing the reagents are such that the contact time with the solid catalyst ranges from 1 second to 300 seconds. In this case, the contact time is determined by the ratio calculated as follows: {volume of catalyst (in liters)×3600}/{[flow rate of the ester or of the acid (in moles/h)+flow rate of ammonia (in moles/h)]×22.4}=contact time in seconds.

In the Mixed Phase

Preferably, the mixed-phase nitrilation process is carried out with the fatty acids.

In the other embodiment (mixed phase), the ammonia is introduced in gas form, whereas the acid is introduced, after optional preheating, into the reactor in proximity to the catalytic bed, at least partly in liquid form at a flow rate determined so as to flow in the form of a film (trickle bed) on the heated catalytic bed on contact with which a fraction of the liquid is vaporized. The reaction or the series of reactions takes place on contact with the surface of the catalyst or in its immediate proximity. This "trickle-bed" technique is well known and widely used in the oil industry. The ammonia stream may be cocurrent or countercurrent with respect to the acid stream.

The acid introduction flow rate is such that the average contact time of the liquid phase in the reactor is less than 1 hour, and preferably less than 30 minutes. This contact time is determined by the following calculation: volume of catalyst (in liters)/acid flow rate (in liquid liters at 25° C. per hour), that is to say the inverse of the liquid hourly liquid volume rate.

In this embodiment, it is possible to work in cocurrent mode, i.e. the gas current and the liquid stream are descending, or in the countercurrent mode, with the gas stream being ascending and the liquid current descending. The latter variant is preferred in the process of the invention. The countercurrent version, with the gas ascending and the acid descending, may be particularly advantageous for limiting the hydrolysis of the nitrile formed. This is because, in this configuration, the ammonia is injected at the bottom, the water and the alcohol leave at the top, the acid enters at the top and the nitrile leaves at the bottom. At the bottom, therefore, the concentration of nitrile and of ammonia is high, and at the top the concentration of water and alcohol is high, and the concentration of ammonia is lower. It is therefore possible to shift the equilibria, in particular that of the hydrolysis of the nitrile, which restores the acid.

Catalyst

A subject of the present invention is also a solid catalyst.

The solid catalyst according to the present invention comprises at least one metal oxide, the metal of which belongs to column 8 of the periodic table, as a mixture with at least one metal oxide chosen from aluminum oxides, zirconium oxides, niobium oxides, tantalum oxides and tin oxides, the metal oxide(s), the metal of which belongs to column 8, being present in a volume ratio of 0.1 to 0.6 relative to the volume of the mixture of all the metal oxides.

Preferably, the metal oxide, the metal of which belongs to column 8 of the periodic table, is an iron oxide. It is in particular chosen from FeO, $Fe_3O_4$ and $Fe_2O_3$. The metal oxide, the metal of which belongs to column 8 of the periodic table, which is preferred is ferric oxide: $Fe_2O_3$.

Preferably, the metal oxides chosen from aluminum oxides, zirconium oxides, niobium oxides, tantalum oxides and tin oxides are chosen from aluminum oxides, zirconium oxides and niobium oxides. More particularly, they are chosen from aluminum oxide: $Al_2O_3$, zirconium oxide $ZrO_2$ and niobium pentoxide: $Nb_2O_5$.

Some of these oxides exist in certain crystallographic forms. Preferably, the alumina used is the gamma-alumina sold by the company BASF under the commercial reference AL-3996, or else by the companies Axens and Sasol.

The zirconia ($ZrO_2$) used is sold by the companies Norpro-St Gobain, Daiichi Kigenso KK, and MEL, the niobium oxide ($Nb_2O_5$) is sold by the companies Starck and CBMM, and the iron III oxide hydrate is sold, inter alia, by the company Sigma-Aldrich (FeO(OH)) (catalyst grade, 30-50 mesh broken and sieved).

Preferably, the solid catalyst according to the invention comprises the following combinations: ferric oxide: $Fe_2O_3$ on a niobium pentoxide support: $Nb_2O_5$; ferric oxide: $Fe_2O_3$ on an aluminum oxide support: $Al_2O_3$, and also ferric oxide: $Fe_2O_3$ on a zirconium oxide support: $ZrO_2$.

The volume ratio of the metal oxide, the metal of which belongs to column 8 of the periodic table, to the volume of the mixture of all the oxides ranges from 0.1 to 0.6.

Preferably, the volume ratio of the iron oxide/alumina oxide pair ranges from 0.2 to 0.5.

Preferably, the volume ratio of the iron oxide/zirconium oxide pair ranges from 0.2 to 0.5.

Preferably, the volume ratio of the iron oxide/niobium oxide pair ranges from 0.2 to 0.5, in particular from 0.25 to 0.4.

Preferably, the catalyst according to the present invention is characterized by a specific surface area ranging from 10 to 500 $m^2/g$, and preferably from 40 to 300 $m^2/g$, more preferentially from 40 to 250 $m^2/g$, and in particular from 40 to 200 $m^2/g$. The term "BET Brunauer, Emmett and Teller) specific surface area" is intended to mean the available surface area per gram of material. This measurement is based on an adsorption of gas at the surface of the solid studied. The measurement of the specific surface area is carried out according to ASTM standard D 3663-84.

Preferably, the catalyst is characterized by a pore size distribution such that less than 20% of the pore volume is in the pores with a diameter of less than 2 nm, and preferably less than 3.5 nm, and even more preferably less than 7 nm. The pore sizes are calculated according to the methods ASTM D4222-83 (by adsorption of nitrogen) for the pore volume distribution measurement and ASTM D4641-87 for the pore size distribution calculation.

The catalyst may be in the form of beads, of extruded objects, of pellets, in cylindrical or polylobe shape, or else in the form of a hollow cylinder with one or more holes, or else in the form of a cylinder having notches along ridges, this being so as to increase the ratio of the external surface area of the grain relative to the volume of the grain. This criterion is important for reducing diffusional limitations.

Preferably, for a catalyst on a fixed bed, the grains have a size of 1 to 8 mm, and preferably of 3 to 5 mm in their industrial use, this dimension being according to their largest length.

Preferably, for a catalysis on a fluidized bed, the grains have an average size of from 40 to 300 μm, and preferably of from 80 to 150 μm, in their industrial use; the catalysts are preferably in the form of microbeads.

Catalyst Preparation Process

Several methods may be suitable as method for preparing the catalysts: coprecipitation of a salt or of a salt mixture; blending of precursors generally in the form of salts, of oxides or of hydroxides; impregnation of one compound with another, for example impregnation of aluminum, zirconium or niobium oxides with a solution containing an iron oxide precursor; reactive milling, in which the two oxides are intimately mixed by high-energy milling, which results in the formation of a new compound; or else atomization. The precursors of the oxides in various forms can be used in particular in oxide, nitrate, carbonate, chloride, sulfate (including oxysulfate), phosphate, organometallic compound, acetate or acetylacetonate form. In the case in point, the preparation of a catalyst from zirconium oxysulfate results in a catalyst suitable for the process of the invention.

The mixing of the metal oxides according to the present invention is preferably mechanical mixing.

According to one embodiment of the invention, the oxides can be separately milled, finely, preferably so as to achieve particle sizes ranging from 1 to 8 mm according to their largest length, and then measured volumes are mixed and homogenized.

Finally, the invention is directed toward the use of the catalyst as defined above, in a process for the nitrilation of fatty acids or of fatty acid esters.

The following examples serve to illustrate the invention without, however, being limiting in nature.

EXAMPLES

The catalysts used in the examples have the following characteristics, which appear in table 1 below:

TABLE 1

| Catalyst | Supplier | BET surface area ($m^2/g$) | Pore volume ($cm^3/g$) |
|---|---|---|---|
| $Al_2O_3$ | BASF | 196 | 0.5 |
| $ZrO_2$ | Norpro St-Gobain | 53 | nc |
| $Fe_2O_3$ | Aldrich | 141 | nc |

Example 1: Test on the Methyl Ester of Lauric Acid

Tests were carried out on the methyl ester of lauric acid.

Procedure:

The assembly consisted of an evaporation chamber, where the ester in its liquid state is continuously fed via a peristaltic pump. A controlled stream of dry nitrogen entrains the ester and transports it to the catalytic bed below. The controlled stream of ammonia encounters the stream of ester+nitrogen flush with the catalytic bed which is a cylinder 8 mm in diameter by 30 mm held on a stainless steel frit. The stream exiting is condensed a first time at 150-170° C. in order to recover the lauric compounds (nitriles, amide, acid, methylamide, etc), and a second time at 12° C. then −77° C. (via a dry ice trap) in order to condense the light compounds. The condensate is removed and analyzed by GC-FID and GC-MS, on the basis of which the concentrations of ester, nitrile and optionally amide and N-methylamide are calculated.

The metal oxides were separately finely milled and then measured volumes were combined and homogenized.

Results:

1. With the $Fe_2O_3$ and $Al_2O_3$ Catalyst

This experiment was carried out with 3 different catalysts: alumina alone: $Al_2O_3$, iron oxide alone: $Fe_2O_3$ and a mixture of $Al_2O$ and $Fe_2O_3$ in an $Fe_2O_3/(Al_2O_3+Fe_2O_3)$ volume ratio of 0.5.

The average residence time is 4.5 seconds. The results in terms of conversion and of nitrilation and relative to the formation of the N-methylated by-product, each expressed as molar percentage, appear in the tables below.

1.1 At 200° C.

TABLE 2

| | $Fe_2O_3/(Al_2O_3 + Fe_2O_3)$ volume ratio | | |
|---|---|---|---|
| | 0.0 | 0.5 | 1 |
| Conversion (mol %) | 18.3 | 21.8 | 7.2 |

TABLE 2-continued

| | $Fe_2O_3/(Al_2O_3 + Fe_2O_3)$ volume ratio | | |
|---|---|---|---|
| | 0.0 | 0.5 | 1 |
| Nitrilation (mol %) | 10.3 | 17.4 | 5.6 |
| N-Methylamide content (mol %) | 0.0 | 0.0 | 0.3 |

It is noted that, even at 200° C., which is a relatively low temperature, the mixture of catalysts according to the invention results in an increase for the nitrilation of 71% calculated relative to the value obtained for the alumina alone, and of 211% calculated relative to the value obtained for the iron oxide alone. Furthermore, there is no formation of N-methylamide.

In addition, compared with the results obtained for the alumina alone, it is noted that the difference obtained between the conversion content and the nitrilation content is much smaller, thus indicating the low by-product content obtained with the catalyst according to the invention.

1.2 At 250° C.

The results appear in table 3 below and in FIG. 1.

TABLE 3

| | $Fe_2O_3/(Al_2O_3 + Fe_2O_3)$ volume ratio | | |
|---|---|---|---|
| | 0.0 | 0.5 | 1 |
| Conversion (mol %) | 52.6 | 76.1 | 38.7 |
| Nitrilation (mol %) | 38.2 | 72.7 | 36.9 |
| N-Methylamide content (mol %) | 1.2 | 1.0 | 0.4 |

These results show a clear improvement in the conversion content and the nitrilation content for the catalyst according to the invention compared with the catalysts alone.

Consequently, for this very short residence time, the tendency obtained at 200° C. is retained, namely good results in terms of conversion and of nitrilation with a very small difference between these two values, indicating a low by-product content. The formation of N-methylamide is limited, and is lower for the mixture of metal oxides than for the pure compounds.

Finally, FIG. 1 provides evidence of the expected effect linked to the values of the volume ratio according to the invention.

2 With the $Fe_2O_3$ et $ZrO_2$ Catalyst

This experiment was carried out with 3 different catalysts: zirconia alone: $ZrO_2$, iron oxide alone: $Fe_2O_3$ and a mixture of $ZrO_2$ and $Fe_2O_3$ in an $Fe_2O_3/(ZrO_2+Fe_2O_3)$ volume ratio of 0.5.

The average residence time is 4.5 seconds. The results in terms of conversion and of nitrilation, each expressed as molar percentage, appear in the tables below.

2.1 At 200° C.

The results appear in table 4 below.

TABLE 4

| | $Fe_2O_3/(ZrO_2 + Fe_2O_3)$ volume ratio | | |
|---|---|---|---|
| | 0.0 | 0.5 | 1 |
| Conversion (mol %) | 55.8 | 43.1 | 7.2 |
| Nitrilation (mol %) | 3.9 | 20.6 | 5.6 |

It is noted that the mixture of catalysts according to the invention results in an increase for the nitrilation compared with the metal oxides used alone.

2.2 At 250° C.

The results appear in table 5 below and in FIG. 2.

TABLE 5

| | $Fe_2O_3/(ZrO_2 + Fe_2O_3)$ volume ratio | | |
|---|---|---|---|
| | 0.0 | 0.5 | 1 |
| Conversion (mol %) | 71.1 | 95.7 | 38.7 |
| Nitrilation (mol %) | 60.2 | 93.4 | 36.9 |

These results show a clear improvement in the conversion content and the nitrilation content for the catalyst according to the invention compared with the catalysts alone.

Consequently, for this very short residence time, good results were observed in terms of conversion and of nitrilation with a very small difference between these two values, indicating a low by-product content.

Finally, FIG. 2 provides evidence of the expected effect linked to the values of the volume ratio according to the invention.

Example 2: Test on the Methyl Ester of Undecenoic Acid

Tests were carried out on the methyl ester of undecenoic acid and with the catalyst $Fe_2O_3$ on an $Al_2O_3$ support. The procedure is the same as that set out in example 1 above.

Results:

This experiment was carried out with 3 different catalysts: alumina alone: $Al_2O_3$, iron oxide alone: $Fe_2O_3$ and an $Al_2O_3/Fe_2O_3$ mixture in an $Fe_2O_3/(Al_2O_3+Fe_2O_3)$ volume ratio of 0.5.

The average residence time is 4.5 seconds. The results in terms of conversion and of nitrilation, each expressed as molar percentage, appear in the tables below.

2.1 At 200° C.

The results appear in table 6 below.

TABLE 6

|  | $Fe_2O_3/(Al_2O_3 + Fe_2O_3)$ volume ratio | | |
| --- | --- | --- | --- |
|  | 0.0 | 0.5 | 1 |
| Conversion (mol %) | 8.7 | 16.5 | 0.7 |
| Nitrilation (mol %) | 1.9 | 9.2 | 0.7 |

It is noted that, even at 200° C., which is a relatively low temperature, the mixture of catalysts according to the invention results in a surprising and unexpected increase in the nitrilation.

2.2 At 250° C.

The results appear in table 7 below.

TABLE 7

|  | $Fe_2O_3/(Al_2O_3 + Fe_2O_3)$ volume ratio | | |
| --- | --- | --- | --- |
|  | 0.0 | 0.5 | 1 |
| Conversion (mol %) | 33.7 | 30.5 | 17.0 |
| Nitrilation (mol %) | 19.0 | 26.6 | 12.0 |

These results show a clear improvement in the nitrilation content for the catalyst according to the invention compared with the catalysts alone.

These tests demonstrate the unexpected and surprising effect provided by the specific catalyst of the invention which comprises a mixture of metal oxides as previously defined, in the ratio of mixtures also previously defined. The degrees of conversion observed, and also the amounts of nitriles observed, are greater than those obtained with the catalysts comprising just one metal oxide. This is all the more surprising since the contact time is very short, evaluated at a few seconds: 4.5 sec.

The invention claimed is:

1. A process for the nitrilation of a fatty acid or of a fatty acid ester to the corresponding nitrile, which is optionally unsaturated, by reacting the fatty acid or fatty acid ester with ammonia in a reactor operating continuously in a gas phase or in a mixed gas-liquid phase in a temperature range of from 180 to 400° C. to produce the corresponding nitrile, in the presence of a solid catalyst comprising:
    at least one metal oxide, the metal of which belongs to column 8 of the periodic table, as a mixture with
    at least one metal oxide selected from the group consisting of aluminum oxides, zirconium oxides, niobium oxides, tantalum oxides and tin oxides,
    the metal oxide(s), the metal of which belongs to column 8 of the periodic table, being present in a volume ratio of 0.1 to 0.6 relative to the volume of the mixture of all the oxides.

2. The process as claimed in claim 1, wherein the catalyst comprises at least as metal oxide, the metal of which belongs to column 8 of the periodic table, ferric oxide.

3. The process as claimed in claim 1, wherein the catalyst comprises ferric oxide ($Fe_2O_3$) and niobium pentoxide ($Nb_2O_5$).

4. The process as claimed in claim 1, wherein the catalyst comprises ferric oxide ($Fe_2O_3$) and aluminum oxide ($Al_2O_3$).

5. The process as claimed in claim 1, wherein the catalyst comprises ferric oxide ($Fe_2O_3$) and zirconium oxide ($ZrO_2$).

6. The process as claimed in claim 1, wherein the fatty acid or fatty acid ester is selected from the group consisting of w-unsaturated acids or esters having the following formula:

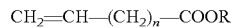

$CH_2=CH-(CH_2)_n-COOR$ in which
n represents the integer 7 or 8 and
R represents either a hydrogen atom or an alkyl radical comprising 1 to 4 carbon atoms.

7. The process as claimed in claim 1, wherein the reaction temperature ranges from 200° C. to 300° C.

8. The process as claimed in claim 1, wherein the reaction temperature ranges from 200° C. to 250° C.

9. The process as claimed in claim 1, which is operated in a gas phase and not in a mixed gas-liquid phase.

10. The process as claimed in claim 1, which is operated in a mixed gas-liquid phase.

11. The process as claimed in claim 1, wherein a fatty acid is reacted.

12. The process as claimed in claim 1, wherein an unsaturated fatty acid ester is reacted and with the absence of isomerization of the double bond thereof.

13. The process as claimed in claim 1, wherein the fatty acid or of a fatty acid ester contains 10 or 11 carbon atoms per molecule.

14. The process as claimed in claim 1, wherein a fatty acid ester is reacted and the fatty acid ester is methyl 9-decenoate or methyl 10-undecenoate.

15. The process as claimed in claim 1, wherein the pressure exerted in the reactor is 0.1 to 10 atmospheres.

16. The process as claimed in claim 1, wherein the ratio of $NH_3$ to fatty acid or fatty acid ester is 1 to 50.

17. The process as claimed in claim 1, which is conducted in the gas phase and the contact time with the solid catalyst is 1 second to 300 seconds.

18. The process as claimed in claim 1, which is conducted in the mixed gas-liquid phase and wherein the average contact time of the liquid phase in the reactor is less than 1 hour.

19. The process as claimed in claim 1, where the catalyst comprises $Fe_2O_3$ and $Al_2O_3$, and wherein the volume ratio of $Fe_2O_3$ to the sum of $Fe_2O_3$ and $Al_2O_3$ is 0.1 to 0.6.

20. The process as claimed in claim 19, wherein the volume ratio of the $Fe_2O_3$ to the sum of the $Fe_2O_3$ and $Al_2O_3$ is 0.2 to 0.5.

* * * * *